United States Patent [19]

Schneider et al.

[11] 4,089,955
[45] May 16, 1978

[54] 7-β-[D-2-AMINO-2-(1,4-CYCLOHEX-ADIENYL)-ACETYLAMINO]-3-HAL-3-CEPHEM-4-CARBOXYLIC ACIDS

[75] Inventors: Peter Schneider, Basel; Hans Bickel, Binningen, both of Switzerland

[73] Assignee: Ciba-Geigy Corporation, Ardsley, N.Y.

[21] Appl. No.: 705,221

[22] Filed: Jul. 14, 1976

[30] Foreign Application Priority Data

Jul. 31, 1975 Switzerland .................. 10001/75

[51] Int. Cl.$^2$ .................. C07D 501/20; A61K 31/545
[52] U.S. Cl. .................................... 424/246; 544/16
[58] Field of Search .................. 260/243 C; 424/246

[56] References Cited

U.S. PATENT DOCUMENTS 3,819,620   6/1974   Djrsch .................................. 544/20
3,925,372  12/1975   Chauvette ........................ 260/243 C

*Primary Examiner*—Nicholas S. Rizzo
*Attorney, Agent, or Firm*—John J. Maitner

[57] ABSTRACT

7β-[D-2-Amino-2-(1,4-cyclohexadienyl)-acetylamino]-3-Hal-3-cephem-4-carboxylic acids, wherein Hal denotes halogen with an atomic number of up to 35, and pharmaceutically acceptable salts thereof are prepared, which compounds have antibiotic activity.

4 Claims, No Drawings

7-β-[D-2-AMINO-2-(1,4-CYCLOHEXADIENYL)-ACETYLAMINO]-3-HAL-3-CEPHEM-4-CARBOXYLIC ACIDS

The invention relates to 7β-[D-2-amino-2-(1,4-cyclohexadienyl)-acetylamino]-3-Hal-3-cephem-4-carboxylic acids (I), wherein Hal denotes halogen with an atomic number of up to 35, or salts thereof, and to processes for their manufacture and also to pharmaceutical formulations containing these compounds as the active compounds, and to their use, preferably in the form of pharmaceutical formulations.

In the abovementioned compounds Hal represents fluorine or bromine but above all represents chlorine.

Salts are, in particular, non-toxic salts which can be used pharmaceutically, such as metal salts or ammonium salts, such as alkali metal salts and alkaline earth metal salts, for example sodium salts, potassium salts, magnesium salts or calcium salts, and also ammonium salts with ammonia or suitable organic amines, and, above all, aliphatic, cycloaliphatic, cycloaliphatic-aliphatic and araliphatic primary, secondary or tertiary mono-, di- or poly-amines, and also heterocyclic bases, can be used for forming the salts, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 2-diethylamino-ethyl 4-aminobenzoate, lower alkyleneamines, for example 1-ethyl-piperidine, cycloalkylamines, for example bicyclohexylamine, or benzylamines, for example N,N'-dibenzyl-ethylenediamine, and also bases of the pyridine type, for example pyridine, collidine or quinoline. The new compounds can also form acid addition salts, for example with inorganic acids, such as hydrochloric acid, sulphuric acid or phosphoric acid, or with suitable organic carboxylic or sulphonic acids, for example trifluoroacetic acid or 4-methylphenylsulphonic acid. The new compounds are preferably in the form of their inner salts, that is to say in the form of the zwitter-ion.

The new compounds of the present invention display valuable antibiotic properties. Thus, in the free form or in the form of their salts, they are active in vitro, in doses of 0.1 to 100 mcg/ml against cocci, for example *Staphylococcus aureus, Staphylococcus faecalis, Diplococcus pneumoniae, Neisseria meningitidis* and *Neisseria gonorrhoeae* and, in doses of 0.4 to 50 mcg/ml, against enterobacteriaceae, for example *Escherichia coli, Klebsiella pneumoniae, Salmonella typhimurium* and *Proteus mirabilis*.

When administered parenterally or, in particular, orally, they are active against micro-organisms, such as Gram-positive bacteria, for example *Staphylococcus aureus, Streptococcus pyogenes* and *Diplococcus pneumoniae* (for example in mice in doses of about 0.0025 to about 0.04 g/kg per os.) and Gram-negative bacteria, for example *Escherichia coli, Salmonella typhimurium, Shigella flexneri, Klebsiella pneumoniae, Proteus vulgaris, Proteus rettgeri* and *Proteus mirabilis* (for example in mice in doses of about 0.008 to about 0.03 g/kg per os.) and especially against penicillin-resistant bacteria, this action being coupled with low toxicity. These new compounds can therefore be used, for example in the form of formulations having an antibiotic action, for the treatment of corresponding infections.

The invention relates above all to 7β-[D-2-amino-2-(1,4-cyclohexadienyl)-acetylamino]-3-chloro-3-cephem-4-carboxylic acid and its salts, especially its non-toxic salts which can be used pharmaceutically and in particular its inner salt. Compared with 7β-(D-2-amino-2-phenyl-acetylamino)-3-chloro-3-cephem-4-carboxylic acid, which is known from U.S. Pat. No. 3,925,372, this compound is distinguished by a greater stability at the physiological pH value.

The new compounds are manufactured in a manner which is in itself known. Thus, for example, they can be obtained when the 3-hydroxyl group in a 7β-[D-2-amino-2-(1,4-cyclohexadienyl)-acetylamino]-3-hydroxy-3-cephem-4-carboxylic acid (II), wherein the carboxyl group is in a protected form and the amino group is preferably in a protected form, is converted into a halogen atom Hal and, if necessary, in a resulting compound, a protected amino group which may be present is converted into the free amino group and/or the protected carboxyl group is converted into the free carboxyl group and, if desired, a resulting salt is converted into the free compound or into another salt and/or a free compound is converted into a salt.

In the above starting material the carboxyl group is in a protected form and the amino group is usually in a protected form, possible protective groups being those used in penicillin and cephalosporin chemistry and in peptide chemistry.

The carboxyl group is usually protected in the esterified form and an ester grouping of this type can be split easily under gentle conditions. Possible suitable protected carboxyl groups are, in particular, lower alkoxycarbonyl, especially tert.-lower alkoxycarbonyl, for example tert.-butoxycarbonyl, polycycloalkoxycarbonyl, for example adamantyloxycarbonyl, arylmethoxycarbonyl, wherein aryl preferably represents one or two phenyl radicals which are optionally monosubstituted or polysubstituted, for example by lower alkyl, especially tert.-lower alkyl, for example tert.-butyl, lower alkoxy, such as methoxy, hydroxyl, halogen, for example chlorine, and/or nitro, such as optionally substituted benzyloxycarbonyl, for example benzyloxycarbonyl substituted as indicated above, for example 4-nitro-benzyloxycarbonyl, or diphenylmethoxycarbonyl which, for example, is substituted as indicated above, for example benzhydryloxycarbonyl or di-(4-methoxyphenyl)-methoxycarbonyl, or 2-halogeno-lower alkoxycarbonyl, for example 2,2,2-trichloroethoxycarbonyl or 2-bromo- or 2-iodo-ethoxycarbonyl, or acylmethoxycarbonyl, especially aroylmethoxycarbonyl, wherein the aroyl group preferably represents benzyl which is optionally substituted, for example by halogen, such as bromine, for example phenacyloxycarbonyl. Esterified carboxyl groups are also corresponding silyloxycarbonyl groups, especially organic silyloxycarbonyl groups. In these groups, the silicon atom preferably has lower alkyl, especially methyl, and lower alkoxy, for example methoxy, and/or halogen, for example chlorine, as substituents. Suitable silyl protective groups are, above all, tri-lower alkylsilyl, especially trimethylsilyl, and also dimethyl-tert.-butyl-silyl, lower alkoxy-lower alkyl-halogeno-silyl, for example methoxy-methyl-chlorosilyl, or di-lower alkyl-halogeno-silyl, for example dimethyl-chloro-silyl. It is also possible for silyl protective groups, and especially those which contain a halogen atom as a substituent, at the same time to protect the carboxyl groups in two different molecules of the starting material; that is to say in such groups the halogen atom has been replaced by the carboxyl group of a further molecule of the starting material.

A preferred protected carboxyl group is, in particular, optionally substituted benzyloxycarbonyl, for example benzyloxycarbonyl which is substituted as mentioned above, for example 4-nitrobenzyloxycarbonyl, or optionally substituted diphenylmethoxycarbonyl, for example diphenylmethoxycarbonyl which is substituted as mentioned above, for example benzhydroloxycarbonyl.

A protected amino group can be, for example, in the form of an acylamino, triarylmethylamino, etherified mercaptoamino, 1-acyl-2-lower alkylideneamino or silylamino group which can be split easily.

In a corresponding acylamino group, acyl is preferably the acyl radical of a carbonic acid half-ester, such as lower alkoxycarbonyl, especially tert.-lower alkoxycarbonyl, for example tert.-butoxycarbonyl, polycycloalkoxycarbonyl, for example adamantyloxycarbonyl, arylmethoxycarbonyl, wherein aryl preferably represents one or two phenyl radicals which are optionally monosubstituted or polysubstituted, for example by lower alkyl, especially tert.-lower alkyl, for example tert.-butyl, lower alkoxy, such as methoxy, hydroxyl, halogen, for example chlorine, and/or nitro, such as optionally substituted benzyloxycarbonyl, for example benzyloxycarbonyl which is substituted as mentioned above, for example 4-nitrobenzyloxycarbonyl, or diphenylmethoxycarbonyl which is substituted, for example as indicated above, for example benzhydryloxycarbonyl or di-(4-methoxyphenyl)-methoxycarbonyl, or 2-halogeno-lower alkoxycarbonyl, for example 2,2,2-trichloroethoxycarbonyl or 2-iodoethoxycarbonyl, or acylmethoxycarbonyl, especially aroylmethoxycarbonyl wherein the aroyl group preferably represents optionally substituted benzoyl, for example benzoyl substituted by halogen, such as bromine, for example phenacyloxycarbonyl. In an acylamino group, acyl can also represent the corresponding radical of an organic sulphonic acid; such a radical is, in particular, arylsulphonyl wherein aryl denotes a phenyl radical which is optionally substituted, for example by lower alkyl, such as methyl, halogen, such as bromine, or nitro, for example 4-methylphenylsulphonyl.

In a triarylmethylamino group, the aryl radicals are, in particular, optionally substituted phenyl radicals; a corresponding group is, above all, trityl.

An etherified mercapto group in an amino group protected by such a radical is, above all, arylthio or aryl-lower alkylthio, wherein aryl is, in particular, phenyl which is optionally substituted, for example by lower alkyl, such as methyl or tert.-butyl, lower alkoxy, such as methoxy, halogen, such as chlorine, and/or nitro. A corresponding amino protective group is, for example, 4-nitrophenylthio.

In a 1-acyl-2-lower alkylidene radical which can be used as an amino protective group, acyl is preferably the corresponding radical of a lower alkanecarboxylic acid, of a benzoic acid which is optionally substituted, for example by lower alkyl, such as methyl or tert.-butyl, lower alkoxy, such as methoxy, halogen, such as chlorine, and/or nitro, or of a carbonic acid half-ester, such as of a carbonic acid lower alkyl half-ester. Corresponding protective groups are, above all, 1-lower alkanoyl-2-propylidene, for example 1-acetyl-2-propylidene, or 1-lower alkoxycarbonyl-2-propylidene, for example 1-ethoxycarbonyl-2-propylidene.

A silylamino group is, above all, an organic silylamino group wherein the silicon atom preferably has lower alkyl, especially methyl, and also lower alkoxy, for example methoxy, and/or halogen, for example chlorine, as substituents. Corresponding silyl groups are, above all, tri-lower alkylsilyl, especially trimethylsilyl, and also dimethyl-tert.-butylsilyl, lower alkoxy-lower alkyl-halogeno-silyl, for example methoxy-methyl-chlorosilyl, or di-lower alkyl-halogeno-silyl, for example dimethyl-chlorosilyl. It is possible for silyl protective groups, especially those which contain a halogen atom as a substituent, at the same time to protect the amino group in two different molecules of the starting material; that is to say in such groups the halogen atom has been replaced by the amino group of a further molecule of the starting material.

The amino group in the starting material II can also be protected in a protonised form; possible anions are, above all, those of strong inorganic acids, such as hydrogen halide acids, for example the chlorine or bromine anion.

Preferred amino protective groups are the acyl radicals of carbonic acid half-esters, especially tert.-lower alkoxycarbonyl, benzyloxycarbonyl or diphenylmethoxycarbonyl, which are optionally substituted, for example as indicated, or 2-halogeno-lower alkoxycarbonyl.

The starting material II is preferably in the indicated 3-hydroxy-3-cephem form but can also be employed in the corresponding tautomeric cepham-3-one form.

The replacement of the hydroxyl group by halogen can be carried out in various ways, usually by treatment with a halogenating, that is to say fluorinating, chlorinating or brominating, agent.

Compounds I wherein Hal denotes fluorine, chlorine or bromine can be manufactured, for example, by treating a starting material II with a phosphorus reagent which replaces enol-hydroxyl groups by halogen and subsequently splitting off the protective groups which are present.

Phosphorus reagents of this type are, for example, dihalogeno-triorganyl-phosphoranes, trihalogeno-diorganyl-phosphoranes or a mixture consisting of a triorganyl-phosphine and a carbon tetrahalide.

In these reagents halogen is fluorine, chlorine or bromine. In the carbon tetrahalide, halogen is preferably chlorine or bromine. The organyl radicals in the phosphoranes and phosphines are organic radicals with up to 18 carbon atoms and can be identical or different.

Organyl radicals are, in particular, hydrocarbon radicals which have up to 18, especially up to 12 and preferably up to 6, carbon atoms and are optionally substituted, for example by tertiary amino groups or polymers, such as lower alkyl radicals, for example methyl, ethyl or propyl, di-lower alkylamino-lower alkyl radicals, for example 3-dimethylaminopropyl, carbocyclic radicals, such as phenyl which is optionally substituted as indicated, and also phenyl which is substituted by polymers, for example by polystyrene cross-linked with divinylbenzene, or phenyl which is substituted by di-lower alkylamino-lower alkyl, for example dimethylaminomethyl. In the case of phenyl substituted by a polymer there is usually only one radical present on a given phosphorus atom.

Further organyl radicals are secondary amino radicals, such as di-lower alkylamino, above all dimethylamino.

Representative examples of the phosphoranes mentioned are difluoro-triphenyl-, trifluoro-diphenyl-, dichloro-triphenyl-, trichloro-diphenyl-, dibromo-triphenyl- and tribromodiphenyl-phosphorane, wherein one of the phenyl groups can be substituted by a polymer, such as a polystyrene crosslinked with divinylbenzene, or by dimethylaminomethyl.

Representative examples of the phosphines mentioned are triethyl-, methyl-propyl-phenyl-, bis-(3-dimethylaminopropyl)-phenyl-, tris-(dimethylamino)-, bis-(dimethylamino)-phenyl- and, in particular, triphenylphosphine, wherein one of the phenyl groups can be substituted by a polymer, such as a polystyrene crosslinked with divinylbenzene.

Carbon tetrahalides are, for example, carbon tetrabromide and, in particular, carbon tetrachloride.

The reaction with the halogenating phosphorus reagents takes place in a manner which is in itself known in an inert aprotic, preferably polar, solvent, such as a chlorinated hydrocarbon, for example methylene chloride, chloroform, carbon tetrachloride of 1,2-dichloroethane, a nitrile, such as acetonitrile or benzonitrile, or a N,N-disubstituted carboxylic acid amide, such as dimethylformamide or N,N-dimethylacetamide, or mixtures thereof, and, depending on the reactivity of the reagent employed, with cooling or warming, that is to say at temperatures between about −60° C and the reflux temperature of the solvent used, and optionally in an inert gas atmosphere, such as a nitrogen atmosphere. When tri-lower alkyl-phosphines or tris-(di-lower alkylamino)phosphines and carbon tetrachloride or carbon tetrabromide are used, cooling is usually necessary, say to −60° to −20° C.

The halogenating phosphoranes mentioned can also be formed in situ, for example by reacting the said phosphines with the desired carbon tetrahalide, in which case other halogenating phosphorus compounds are also formed in addition to the dihalogeno-triorganyl phosphorane, or by treating the phosphines with a halogen, for example chlorine, or by reacting triorganylphosphine oxides with a dihalogenocarbonyl, such as phosgene, or trihalogenosilane, such as trichlorosilane.

When halogenating with the said phosphoranes, a weak base, such as pyridine or a N,N-di-lower alkylaniline, such as N,N-dimethylaniline, can be added to the reaction medium in order to take up the hydrogen halide formed.

In a preferred embodiment, the carbon tetrahalide is added, preferably in excess, to a starting material II in one of the inert aprotic solvents mentioned, such as methylene chloride, at room temperature, that is to say about 20°-25° C, and triphenylphosphine is then added in amounts of about 1.2 to 2 equivalents of the starting material and the reaction mixture is left to stand, or is stirred, at the same temperature until the halogenation is complete.

Compounds I wherein Hal denotes chlorine or bromine can be obtained, for example, by treating the starting material II with a corresponding N,N-disubstituted halogeno-iminium halide compound, especially of the formula

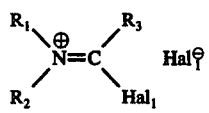 (III)

and subsequently splitting off protective groups which are present. In the formula III, $R_1$ and $R_2$ represent organic, for example aliphatic, radicals, above all lower alkyl and especially methyl, and $R_3$ represents, in particular, hydrogen but can also be an organic, for example aliphatic, radical, such as lower alkyl, and especially methyl, whilst $Hal_1$ is chlorine or bromine.

The above reagent is usually manufactured in situ by treating a suitable N,N-disubstituted amide of the formula

 (IV)

wherein $R_1$, $R_2$ and $R_3$ have the abovementioned meanings, especially a corresponding N,N-disubstituted formamide and above all dimethylformamide, with one of the chlorinating or brominating agents customarily used. The latter are suitable carbonic acid halides, for example phosgene, or carbonyl dibromide, carboxylic acid halides, for example oxalyl chloride or oxalyl bromide, sulphuric acid halides, for example thionyl chloride or thionyl bromide, or phosphoric acid chlorides, for example phosphorus trichloride, phosphorus oxychloride, phosphorus tribromide or phosphorus oxybromide, and also phosphorus pentachloride. Particular chlorinating and brominating agents are phosphorus trichloride and phosphorus tribromide.

The above reaction is usually carried out in the presence of a solvent or diluent and it is usually possible to use, as the solvent or diluent, an amide of the formula IV which is also suitable as a solvent, especially dimethylformamide, which preferably is in the anhydrous form. In addition to the amide, which is usually present in excess and serves as the solvent and is customarily dimethylformamide and also dimethylacetamide, it is also possible correspondingly to use ether-like solvents, for example tetrahydrofurane or dioxane, halogenated hydrocarbons, for example methylene chloride, or sulphoxides, for example dimethylsulphoxide.

The abovementioned chlorinating and brominating agents are customarily used in amounts which correspond to two equivalents of the 3-hydroxy-3-cephem starting material. The reaction can, for example, be so carried out that the chlorinating or brominating agent is added to a solution of the 3-hydroxy-3-cephem starting material is an amide of the formula IV, especially in dimethylformamide. During the addition, this solution is kept at a temperature of about 0° C to about 15° C and thereafter the reaction mixture is left to stand for several hours at room temperature. Initially, the reaction is exothermic; the reaction vessel must therefore be so cooled that the temperature in this reaction phase can be kept below about 25° C. The reaction mixture is then left to stand at about room temperature for the remainder of the reaction period and it is possible to follow the course of the reaction by thin layer chromatography.

The chlorination or bromination can also be carried out by first mixing the chlorinating or brominating agent with the amide of the formula IV, especially dimethylformamide, by which means the halogenoiminium halide of the formula III is formed, and then reacting the latter with a solution of the 3-hydroxy-3-cephem starting material II in the amide, especially in dimethylformamide, to which an additional solvent can also be added, or in another solvent, for example tetrahydrofurane. If necessary, the reactions are carried out in an inert gas atmosphere.

The conversion of the 3-hydroxyl group into fluorine can be effected, for example, by treating the starting material II with a reagent of the formula $F_3S-Am$, wherein Am represents a disubstituted amino group; such reagents have been described, inter alia, by Markovsky et al., Synthesis, Volume 1973, page 787. The amino group preferably contains, as substituents, two monovalent, optionally substituted, preferably aliphatic, but also aromatic, hydrocarbon radicals or one divalent, optionally substituted, preferably aliphatic hydrocarbon radical. Monovalent aliphatic hydrocarbon radicals are, above all, lower alkyl, for example methyl, ethyl, n-propyl, isopropyl or straight-chain or branched butyl, whilst corresponding aromatic hydrocarbons are preferably optionally substituted phenyl, for example phenyl substituted by lower alkyl, such as methyl, lower alkoxy, such as methoxy, and/or halogen, for example chlorine. In a divalent aliphatic hydrocarbon radical, carbon atoms can optionally be replaced by hetero-atoms, such as an oxygen or an optionally substituted nitrogen atom; such divalent radicals are lower alkylene, for example 1,4-butylene or 1,5-pentylene, oxa-lower alkylene, for example 3-oxa-1,5-pentylene, or aza-lower alkylene which is optionally N-substituted by lower alkyl, for example 3-methyl-3-aza-1,5-pentylene. The group $Am$ therefore above all represents di-lower alkylamino, for example dimethylamino, diethylamino, ethyl-methyl-amino, methyl-propyl-amino, di-n-propylamino or diisopropylamino, lower alkyl-phenyl-amino, for example methyl-phenyl-amino or ethyl-phenyl-amino, lower alkyleneamino, for example pyrrolidino or piperidino, oxa-lower alkyleneamino, for example morpholino, or amino which is optionally substituted by aza-lower alkyl, for example 4-methyl-piperazino.

The above reaction is preferably carried out in the presence of a suitable inert solvent and the solvents used are, for example, optionally substituted carbocyclic hydrocarbons, for example alicyclic hydrocarbons, such as cyclopentane, cyclohexane, cycloheptane or decahydronaphthalene, or aromatic carbocyclic hydrocarbons, such as benzene, toluene or xylenes, which can also be halogenated on the nucleus, such as chlorobenzene, dichlorobenzenes or bromobenzene, and especially saturated aliphatic hydrocarbons, such as pentanes, hexanes, heptanes or octanes, or corresponding halogenated, and especially chlorinated, hydrocarbons, such as chloroform, 1,1- or 1,2-dichloroethane, 1,1-, 1,2- or 1,3-dichloropropane and, above all, methylene chloride. Further solvents which can also be used are aliphatic, and especially cyclic, ethers, such as diethyl ether, diisopropyl ether, ethylene glycol dimethyl ether, tetrahydrofurane and, above all, dioxane, and also nitrogen-containing aromatic heterocyclic compounds, such as pyridine and its homologues or quinoline. Optionally, an excess of the fluorinating agent can be used as the solvent and/or several of the solvents mentioned can be combined with one another.

The reaction is, if necessary, carried out with cooling or warming, for example in a temperature range from about $-20°$ C to about $80°$ C, preferably from about $0°$ C to about $30°$ C, and/or under an inert gas atmosphere.

A fluorine atom can also be introduced when the starting material used is a starting material II in which the hydroxyl group is in the form of an organic sulphonyloxy group, that is to say when a 7$\beta$-[D-2-amino-2-(1,4-cyclohexadienyl)-acetylamino]-3-sulphonyloxy-3-cephem-4-carboxylic acid (IIa), wherein the carboxyl group is in the protected form and the amino group is preferably in the protected form and the sulphonyloxy group represents an organic sulphonyloxy group, is reacted with an organic fluoride in the presence of a crown ether and, if necessary and desired, the additional process steps are carried out.

An organic sulphonyloxy group is, above all, lower alkylsulphonyloxy, especially methylsulphonyloxy, but can also by arylsulphonyloxy wherein aryl is preferably phenyl which is optionally substituted, for example by lower alkyl, such as methyl, halogen, for example bromine, or nitro, for example 4-methyl-phenylsulphonyloxy.

An inorganic fluoride is, above all, a metal fluoride and, in particular, an alkali metal fluoride, for example sodium fluoride, or a heavy metal fluoride, for example silver fluoride, is used.

The crown ethers which are used together with the inorganic fluoride are optionally substituted 18-coronene 6-ethers, such as dicyclohexyl-18-crown-6-ether.

The reaction is carried out in the presence of an inert solvent, especially a nitrile, for example acetonitrile or propionitrile, or a nitro-lower alkane, for example nitromethane or nitroethane, under essentially anhydrous conditions and, if necessary, with cooling, for example in a temperature range of from about $-20°$ C to about $25°$ C, preferably at about room temperature, and optionally in an inert gas atmosphere.

The 3-sulphonyloxy-3-cephem starting material (IIa) can also be formed in situ since any 7$\beta$-[D-2-amino-2-(1,4-cyclohexadienyl)-acetylamino]-3-sulphonyloxy-2-cephem-4$\xi$-carboxylic acid (IIb) which may be present together with the starting material IIa and wherein the carboxyl group is in a protected form and the amino group is preferably in a protected form and the sulphonyloxy group represents an organic sulphonyloxy group is converted, under the reaction conditions, into the corresponding 3-sulphonyloxy-3-cephem starting material IIa and enters as such into the reaction with the fluorinating agent.

The starting material II is known and can be manufactured, for example, by acylating the amino group in a 7$\beta$-amino-3-hydroxy-3-cephem-4-carboxylic acid (V), wherein the carboxyl group is in the protected form and especially in an esterified form, with a D-2-amino-2-(1,4-cyclohexadienyl)-acetyl radical. The acylation can be carried out, for example, by the method described below and, below, the amino group in the acylating agent is preferably in a protected form. The hydroxyl group in the enol grouping can be converted into the sulphonyloxy group, for example by treatment with an organic sulphonic acid halide, for example a sulphonic acid chloride, in the presence of a tertiary amine, such as triethylamine, or of dimethylformamide and propylene oxide.

The new compounds can also be obtained when the amino group in a 7$\beta$-amino-3-Hal-3-cephem-4-carboxylic acid (VI), wherein the carboxyl group is preferably in a protected form and the amino group is optionally in a reactive, protected form, is acylated with a D-2-amino-2-(1,4-cyclohexadienyl)-acetyl radical, wherein the amino group is optionally in a protected form, and any protective groups which are present are subsequently split off.

In the starting material VI, the carboxyl group can preferably be in an esterified form, for example as described above. The carboxylic acid starting material VI can, however, also be used in the form of a salt, for example in the form of an ammonium salt, such as a salt with triethylamine, or in the form of a compound which has a carboxyl group protected by reaction with a suitable organic phosphorus halide compound, such as with a lower alkyl- or lower alkoxy-phosphorus dihalide, such as methylphosphorus dichloride, ethylphosphorus dibromide or methoxyphosphorus dichloride. An amino group in a reactive protected form is, for example, an amino group protected by a silyl radical, such as one of the corresponding radicals mentioned above.

The acylation of the free or reactive protected amino group in the starting material VI is carried out in a manner which is in itself known. Acylating agents which can be used are D-2-amino-2-(1,4-cyclohexadienyl)-acetic acid (VII) or a reactive derivative thereof and the amino group can usually be in a protected form, inter alia also in a protonised form.

If the free acid (VII) with a protected amino group is employed for the acylation, suitable condensing agents, such as carbodiimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyldiimidazole, or isoxazolinium salts, for example N-ethyl-5-phenyl-isoxazolinium 3'-sulphonate and N-tert.-butyl-5-methyl-isoxazolinium perchlorate, or a suitable acylamino compound, for example 2-ethoxy-1-ethoxycarbonyl-1,2-dihydroquinoline, are customarily used. The condensation reaction is preferably carried out in an anhydrous reaction medium, for example in methylene chloride, dimethylformamide or acetonitrile.

A functional derivative of the said acid VII, which usually has a protected amino group, is above all an anhydride thereof, including, and preferably, a mixed anhydride. Mixed anhydrides are, for example, those with inorganic acids, especially with hydrogen halide acids, that is to say the corresponding acid halides, for example the acid chloride or acid bromide, and also the anhydride with hydrazoic acid, that is to say the corresponding acid azide, with a phosphorus-containing acid, for example phosphoric acid or phosphorous acid, with a sulphur-containing acid, for example sulphuric acid, or with hydrocyanic acid. Further mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl or isobutyl half-ester of carbonic acid, or with organic, and especially aliphatic or aromatic, sulphonic acids, for example p-toluene-sulphonic acid.

Further acid derivatives which are suitable for reaction with the free amino group are activated esters of the said acid VII, which usually has a protected amino group, such as esters with vinylogous alcohols (that is to say enols), such as vinylogous lower alkanols, or aryl esters, such as phenyl esters which are preferably substituted, for example by nitro or halogen, such as chlorine, for example pentachlorophenyl, 4-nitrophenyl or 2,4-dinitrophenyl esters, heteroaromatic esters, such as benztriazole esters, or diacyliminoesters, such as succinylimino- or phthalylimino-esters.

The acylation with an acid derivative, such as an anhydride and especially with an acid halide, can be carried out in the presence of an acid-binding agent, for example an organic base, such as an organic amine, for example a tertiary amine, such as a tri-lower alkylamine, for example triethyl-amine, a N,N-di-lower alkyl-aniline, for example N,N-dimethyl-aniline, or a base of the pyridine type, for example pyridine, an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or an oxirane, for example a lower 1,2-alkylene oxide, such as ethylene oxide or propylene oxide.

The above acylation can be carried out in an aqueous, or preferably non-aqueous, solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof and, if necessary, at reduced or elevated temperature and optionally in an inert gas atmosphere, for example a nitrogen atmosphere.

The starting materials (VI) are known and can be manufactured, for example, by splitting the acylamino grouping in 7$\beta$-acylamino-3-Hal-3-cephem-4-carboxylic acid compounds, wherein aryl denotes a radical which differs from the D-2-amino-2-(1,4-cyclohexadienyl)-acetyl radical, for example phenylacetyl or phenoxyacetyl, in a manner which is in itself known, for example by treatment with phosphorus pentachloride in the presence of pyridine, followed by methanol and then, optionally, water.

The protected carboxyl and/or amino groups in the compounds obtainable according to the invention are optionally liberated together in a manner which is in itself known, such as by means of solvolysis, including hydrolysis, alcoholysis or acidolysis, or by means of reduction, including hydrogenolysis or chemical reduction.

Thus, for example, a tert.-lower alkoxycarbonyl, polycycloalkoxycarbonyl or diphenylmethoxycarbonyl group can be converted into a free carboxyl group by treatment with a suitable acid agent, such as formic acid or trifluoroacetic acid, optionally with the addition of a nucleophilic compound, such as phenol or anisole. An optionally substituted benzyloxycarbonyl group can be liberated, for example, by means of hydrogenolysis by treatment with hydrogen in the presence of a hydrogenation catalyst, such as a palladium catalyst. Furthermore, certain substituted benzyloxycarbonyl groups, such as 4-nitrobenzyloxycarbonyl, can also be converted into a free carboxyl group by means of chemical reduction, for example by treatment with a chemical reducing agent, such as a metal, for example zinc, or a reducing metal salt, such as a chromium-II salt, for example chromium-II chloride, usually in the presence of a hydrogen donor which, together with the metal, is able to produce nascent hydrogen, such as an acid, above all acetic acid and also formic acid, or of an alcohol, in which case water is preferably added. It is also possible, in the same way, to convert a 2-halogeno-lower alkoxycarbonyl group (optionally after converting a 2-bromo-lower alkoxycarbonyl group into a 2- iodo-lower alkoxycarbonyl group) or an acylmethoxycarbonyl group into a free carboxyl group and an aroylmethoxycarbonyl group can also be converted by treatment with a nucleophilic, preferably salt-forming, reagent, such as sodium thiophenolate or sodium iodide. A carboxyl group which, for example, is protected by silylation can be liberated in the customary manner, for example by treatment with water or an alcohol. Analogously, a carboxyl group protected by reaction with an organic phosphorus halide compound can also be liberated by hydrolysis or alcoholysis.

A protected amino group is liberated in a manner which is in itself known and, depending on the nature of the protective group, in diverse ways, for example by means of solvolysis or reduction. A 2-halogeno-lower alkoxycarbonylamino group (optionally after converting a 2-bromo-lower alkoxycarbonyl group into a 2-iodo-lower alkoxycarbonyl group), an acylmethoxycarbonylamino group or, for example, a 4-nitrobenzyloxycarbonylamino group can, for example, be liberated by treatment with a suitable chemical reducing agent, such as zinc in the presence of aqueous acetic acid, or under basic conditions, for example in the presence of alkali metal hydroxides or secondary or tertiary amines with 1 to 6 equivalents of an alkali metal dithionite, for example sodium dithionite, a diphenylmethoxycarbonylamino, tert.-butyl-lower alkoxycarbonylamino or polycycloalkoxycarbonylamino group can, for example, be liberated by treatment with formic acid or trifluoroacetic acid, an optionally substituted benzyloxycarbonylamino group can, for example, be liberated by means of hydrogenolysis by treatment with hydrogen in the presence of a hydrogenation catalyst, such as a palladium catalyst, an arylthioamino group or aryl-lower alkylthioamino group can, for example, be liberated by treatment with a nucleophilic reagent, such as sulphurous acid, an arylsulphonylamino group can, for example, be liberated by means of electrolytic reduction, a 1-acyl-2-lower alkylideneamino group or a triarylmethyl group can, for example, be liberated by treatment with an aqueous mineral acid and an amino group protected by an organic silyl group can, for example, be liberated by means of hydrolysis or alcoholysis.

Salts of the new compounds can be manufactured in a manner which is in itself known. Thus, salts can be formed, for example, by treatment with metal compounds, such as alkali metal salts of suitable carboxylic acids, for example the sodium salt of α-ethyl-caproic acid, or with ammonia or a suitable organic amine and, preferably, stoichiometric amounts, or only a small excess, of the salt-forming agent are used. Acid addition salts are obtained in the customary manner, for example by treatment with an acid or a suitable anion exchange reagent. Inner salts can be formed, for example, by neutralisation of, for example, salts, such as acid addition salts, to the isoelectric point, for example with weak bases, or by treatment with liquid ion exchangers.

Salts can be converted into the free compounds in the customary manner, metal salts and ammonium salts being converted, for example by treatment with suitable acids and acid addition salts being converted, for example, by treatment with a suitable basic agent.

The process also includes those embodiments according to which compounds obtained as intermediate products are used as starting materials and the remaining process steps are carried out with these, or the process is discontinued at any stage; furthermore, starting materials can be used in the form of derivatives or can be formed during the reaction.

Preferably, the starting materials used and the reaction conditions chosen are such that the compounds mentioned initially as being particularly preferred are obtained.

The new compounds of the present invention can, for example, be used to manufacture pharmaceutical formulations which contain an effective amount of the active substance together with, or mixed with inorganic or organic, solid or liquid excipients which can be used pharmaceutically and which are suitable for enteral or parenteral administration. Thus, tablets or gelatine capsules which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol are used; tablets also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone, and, if desired, disintegrating agents, for example starches, agar or alginic acid or a salt thereof, such as sodium alginate, and/or effervescent mixtures, or adsorbents, dyestuffs, flavourings and sweeteners. Furthermore, the new pharmacologically active compounds can be used in the form of injectable formulations, for example formulations which can be administered intravenously, or of infusion solutions. Such solutions are preferably isotonic aqueous solutions or suspensions and these can be prepared before use, for example from lyophilised preparations which contain the active compound on its own or together with an excipient, for example mannitol. The pharmaceutical formulations can be sterilised and/or contain auxiliaries, for example preservatives, stabilisers, wetting agents and/or emulsifiers, solubilising agents, salts for regulating the osmotic pressure and/or buffers. The present pharmaceutical formulations which, if desired, can contain further pharmacologically valuable substances, are manufactured in a manner which is in itself known, for example by means of conventional mixing, granulating, dragee-making, dissolving or lyophilising processes and contain from about 0.1% to 100%, and especially from about 1% to about 50%, of the active compound and lyophilisates contain up to 100% of the active compound. The individual dose for a warm-blooded animal weighing about 70 kg is between 0.1 and 0.75 g and the daily dose is between 0.2 and 1.0 g.

In the context of the present description, the organic radicals designated as "lower" contain, where they are not expressly defined, up to 7 and preferably up to 4 carbon atoms.

The examples which follow serve to illustrate the invention; the temperatures are given in degrees centigrade.

EXAMPLE 1 a. 100 ml of dimethylformamide are cooled to 0° C and 4.9 ml (66.6 mmols) of thionyl chloride are added slowly. 9.75 g (16.7 mmoles) of benzhydryl 7β-[D-2-(tert.-butoxy-carbonylamino)-2-(1,4-cyclohexadienyl)-acetylamino[-3-hydroxy-3-cephem-4-carboxylate are added, in portions, to this solution under $N_2$ and the temperature is brought slowly to 25° C. After stirring for 4 hours at room temperature and under $N_2$, a further 2.5 ml of thionyl chloride are added. After a total reaction period of 4½ hours, the crude product is poured onto about 500 ml of ice and 400 ml of ethyl acetate, the mixture is diluted with 500 ml of water and the organic phase is separated off. The organic phase is washed with five times 700 ml of water and a little saturated NaCl solution. The aqueous phases are extracted twice more with ethyl acetate and the combined ethyl acetate solutions are dried over sodium sulphate and concentrated. The crude product is subjected to column chromatography (20 times the amount of silica gel, system: toluene/ethyl acetate, 4:1). The corresponding fractions containing benzhydryl 7$\beta$-[D-2-(tert.butoxycarbonylamino)-2-(1,4-cyclohexadienyl)-acetylamino]-3-chloro-3-cephem-4-carboxylate ($R_f$ = 0.4, silica gel, toluene/ethyl acetate, 3:1) are combined and employed in the next reaction step.

For further purification, the crude product can be made to crystallise from methylene chloride/diethyl ether and crystals which have a melting point of 158°–160° C are obtained; UV spectrum (ethanol): $\lambda_{max}$ = 268 nm ($\epsilon$ = 7,400); IR spectrum (CH$_2$Cl$_2$): bands at 2.95, 5.57, 5.8, 5.9 and 6.70 $\mu$.

ai. It is also possible to employ 35 mmols of phosphorus trichloride in place of 66.6 mmols of thionyl chloride.

b. 1.57 g (2.6 mmols) of benzhydryl 7$\beta$-[D-2-(tert.-butoxycarbonylamino)-2-(1,4-cyclohexadienyl)-acetylamino]-3-chloro-3-cephem-4-carboxylate are suspended in 2 ml of anisole at 0° C and 10 ml of trifluoroacetic acid are added. After stirring for 15 minutes at 0° C, the solution is diluted with toluene and then concentrated to about 5 g in vacuo. It is then partitioned between water and ethyl acetate and the organic phase is washed once with water. The pH of the combined aqueous phases is adjusted to a pH of 4.8 with triethylamine, whereupon the inner salt of 7$\beta$-[D-2-amino-2-(1,4-cyclohexadienyl)-acetylamino]-3-chloro-3-cephem-4-carboxylic acid crystallises out as the dihydrate; melting point 160° C (decomposition); UV spectrum (0.1 N HCl): $\lambda_{max}$ = 267 nm ($\epsilon$ = 7,700); IR spectrum (Nujol): bands at 2.98, 5.6, 5.76, 6.2 and 6.64 $\mu$.

The starting material can be obtained as follows:

c. 2.17 g (4.16 mmols) of benzhydryl 7$\beta$-amino-3-hydroxy-3-cephem-4-carboxylate are dissolved in 32 ml of methylene chloride (anhydrous) and the solution is then stirred with 1.53 ml (6.3 mmols) of bis-trimethylsilyl-acetamide at room temperature for 40 minutes under N$_2$ (solution I). A further solution (II) of 1.77 g (7 mmols) of D-2-tert.-butoxy-carbonylamino-2-(1,4-cyclohexadienyl)-acetic acid in 75 ml of methylene chloride is stirred with 0.78 ml (7.0 mmols) of N-methyl-morpholine and 0.91 ml (7.0 mmols) of isobutyl chloroformate for 30 minutes at 0° C under nitrogen. Solution I is cooled to −10° C and solution II is added slowly. The reaction mixture is stirred for 30 minutes at −10° C and for 30 minutes at 0° C, 100 ml of water are added and the phases are separated. The organic solution is washed with a saturated aqueous solution of sodium chloride, dried over sodium sulphate and concentrated. The residue is purified by means of preparative layer chromatography (silica gel, system: toluene/ethyl acetate, 3:1, Rf about 0.15). Benzhydryl 7$\beta$-[D-2(tert.-butoxycarbonylamino)-2-(1,4-cyclohexadienyl)-acetylamino[-3-hydroxy-3-cephem-4-carboxylate, which according to thin layer chromatography is a single compound, is obtained as an amorphous product.

EXAMPLE 2

420 mg (1.6 mmols) of triphenylphosphine are added, at room temperature and under a nitrogen atmosphere, to a solution of 617 mg (1 mmol) of benzhydryl 7$\beta$-[D-2-(tert.-butoxy-carbonylamino)-2-(1,4-cyclohexadienyl)-acetylamino]-3-hydroxy-3-cephem-4-carboxylate in a mixture of 1 ml of carbon tetrachloride and 20 ml of methylene chloride. The reaction mixture is left to stand at room temperature for 24 hours and then washed with water and a saturated aqueous solution of sodium chloride. The organic phase is dried over sodium sulphate and evaporated in vacuo. The residue is chromatographed on silica gel using toluene/ethyl acetate, 3:1. The fractions containing benzhydryl 7$\beta$-[D-2-(tert.-butoxy-carbonylamino)-2-(1,4-cyclohexadienyl)-acetylamino[-3-chloro-3-cephem-4-carboxylate are combined and crystallised from methylene chloride/diethyl ether. The resulting crystals having a melting point of 158°–160° C.

EXAMPLE 3

460 mg (1.3 mmols) of dichloro-triphenyl-phosphorane and 0.08 ml (1 mmol) of pyridine are added, at room temperature and under a nitrogen atmosphere, to a solution of 617 mg (1 mmol) of benzhydryl 7$\beta$-[D-2-(tert.-butoxycarbonylamino)-2-(1,4-cyclohexadienyl)-acetylamino]-3-hydroxy-3-cephem-4-carboxylate in 10 ml of methylene chloride. The reaction mixture is left to stand at room temperature for 24 hours and then washed with water and a saturated aqueous solution of sodium bicarbonate. The organic phase is dried over sodium sulphate and evaporated in vacuo. The residue is chromatographed on silica gel using toluene/ethyl acetate, 3:1. The fractions containing benzhydryl 7$\beta$-[D-2-(tert.-butoxycarbonylamino)-2-(1,4-cyclohexadienyl)-acetylamino]-3-chloro-3cephem-4- carboxylate are combined and crystallised from methylene chloride/diethyl ether. The resulting crystals have a melting point of 158°–160° C.

EXAMPLE 4

A solution, which has been cooled to 0° C, of 0.253 g (1 mmol) of D-$\alpha$-tert.-butoxycarbonylamino-$\alpha$-(1,4-cyclohexadienyl)-acetic acid in 75 ml of methylene chloride is stirred with 0.097 ml of N-methyl-morpholine and 0.129 ml of isobutyl chloroformate under a nitrogen atmosphere for 30 minutes, the mixture is then cooled to −10° and 0.33 g of benzhydryl 7$\beta$-amino-3-chloro-3-cephem-4-carboxylate and 0.085 ml of N-methyl-morpholine are added successively. The reaction mixture is stirred for 30 minutes at −10° C and for 30 minutes at 0° C, 30 ml of water are added and the pH value is adjusted to 7.9 by adding a 40% strength aqueous solution of dipotassium hydrogen phosphate. The phases are separated, the aqueous solution is extracted with methylene chloride and the combined organic solutions are washed with a saturated solution of sodium chloride, dried over sodium sulphate and evaporated under reduced pressure. The residue is purified by means of preparative layer chromatography (silica gel, system: toluene/ethyl acetate, 3:1, Rf about 0.4). Benzhydryl 7$\beta$-[D-2-(tert.-butoxycarbonylamino)-2-(1,4-cyclohexadienyl)-acetylamino]-3-chloro-3-cephem-4-carboxylate, which according to thin layer chromatography is a single compound, is obtained as an amorphous product which can be further used analogously to Example 1.

EXAMPLE 5

0.4 ml of bis-(trimethylsilyl)-acetamide is added to a suspension of 323 mg (1.38 mmols) of 7β-amino-3-chloro-3-cephem-4-carboxylic acid in 10 ml of methylene chloride and the mixture is stirred for 1 hour at room temperature. The solution, which is then clear, is cooled to −10° C and 0.315 g (1.52 mmols) of 2-(1,4-cyclohexadienyl)-glycyl chloride-hydrochloride is added. The reaction mixture is stirred at the same temperature for 1 hour and 20 ml of water are then added. The aqueous phase is washed with about 20 ml of methylene chloride and the pH value is raised to 5.5 by adding 1 N sodium hydroxide solution. After concentrating the aqueous phase, the inner salt of 7β-[D-2-amino-(1,4-cyclohexadienyl)-acetylamino]-3-chloro-3-cephem-4-carboxylic acid crystallises out as the dihydrate. The melting point, the UV spectrum and the IR spectrum correspond to the values given in Example 1b.

EXAMPLE 6

7β-[D-2-Amino-2-(1,4-cyclohexadienyl)-acetylamino]-3-fluoro-3-cephem-4-carboxylic acid and 7β-[D-2-amino-2-(1,4-cyclohexadienyl)-acetylamino]-3-bromo-3-cephem-4-carboxylic acid, or their salts, especially their inner salts, can be manufactured in the manner described and illustrated above.

EXAMPLE 7

Dry ampoules or phials containing 0.5 g of the inner salt of 7β-[D-2-amino-2-(1,4-cyclohexadienyl)-acetylamino]-3-chloro-3-cephem-4-carboxylic acid are manufactured as follows:

| Composition (for 1 ampoule or phial) | |
| --- | --- |
| inner salt of 7β-[D-2-amino-2-(1,4-cyclohexadienyl)-acetylamino]-3-chloro-3-cephem-4-carboxylic acid | 0.5 g |
| mannitol | 0.05 g |

A sterile aqueous solution of the inner salt of 7β-[D-2-amino-2-(1,4-cyclohexadienyl)-acetylamino]-3-chloro-3-cephem-4-carboxylic acid and mannitol is subjected to freeze-drying under aseptic conditions in 5 ml ampoules or 5 ml phials and the ampoules or phials are sealed and tested.

EXAMPLE 8

Capsules containing 0.25 g of the inner salt of 7β-[D-2-amino-2-(1,4-cyclohexadienyl)-acetylamino]-3-chloro-3-cephem-4-carboxylic acid are manufactured as follows:

| Composition (for 4,000 capsules) | |
| --- | --- |
| inner salt of 7β-[D-2-amino-2-(1,4-cyclohexadienyl)-acetylamino]-3-chloro-3-cephem-4-carboxylic acid | 250,000 g |
| maize starch | 50,000 g |
| polyvinylpyrrolidone | 15,000 g |
| magnesium stearate | 5,000 g |
| ethanol | q.s. |

The inner salt of 7β-[D-2-amino-2-(1,4-cyclohexadienyl)-acetylamino]-3-chloro-3-cephem-4-carboxylic acid and the maize starch are mixed and the mixture is moistened with a solution of polyvinylpyrrolidone in 50 g of ethanol. The moist mass is pressed through a sieve which has a mesh width of 3 mm and dried at 45°. The dry granules are forced through a sieve which has a mesh width of 1 mm and mixed with 5 g of magnesium stearate. The mixture is filled, in portions of 0.320 g, into size 0 push-fit capsules.

What is claimed is:

1. A 7β-[D-2-amino-2-(1,4-cyclohexadienyl)-acetylamino[-3-Hal-3-cephem-4-carboxylic acid (I) in which Hal denotes halogen with an atomic number of up to 35, or a pharmaceutically acceptable salt thereof.

2. A compound according to claim 1, which is 7β-[D-2-Amino-2-(1,4-cyclohexadienyl)-acetylamino]-3-chloro-3-cephem-4-carboxylic acid or a pharmaceutically acceptable salt thereof.

3. A pharmaceutical composition comprising an antibiotically effective amount of a compound according to claim 1 and a pharmaceutical carrier.

4. A method for the treatment of infectious diseases, which comprises administering to the infected host an antibiotically effective amount of a compound according to claim 1.

* * * * *